US010955398B2

(12) United States Patent
Mizutani et al.

(10) Patent No.: US 10,955,398 B2
(45) Date of Patent: Mar. 23, 2021

(54) CALIBRATION METHOD FOR GAS ANALYSIS APPARATUS, GAS ANALYSIS SYSTEM, AND PRESSURE VARYING DEVICE

(71) Applicant: HORIBA, Ltd., Kyoto (JP)

(72) Inventors: Naoto Mizutani, Kyoto (JP); Takeshi Kusaka, Kyoto (JP); Haruhisa Mohara, Kyoto (JP); Masayoshi Shinohara, Kyoto (JP)

(73) Assignee: HORIBA, LTD., Kyoto (JP)

( * ) Notice: Subject to any disclaimer, the term of this patent is extended or adjusted under 35 U.S.C. 154(b) by 112 days.

(21) Appl. No.: 16/181,469

(22) Filed: Nov. 6, 2018

(65) Prior Publication Data
US 2019/0137465 A1 May 9, 2019

(30) Foreign Application Priority Data

Nov. 6, 2017 (JP) .............................. JP2017-214121

(51) Int. Cl.
| | |
|---|---|
| *G01N 33/00* | (2006.01) |
| *G01N 21/27* | (2006.01) |
| *G01N 21/3504* | (2014.01) |
| *G01M 15/10* | (2006.01) |
| *G01N 1/22* | (2006.01) |

(52) U.S. Cl.
CPC ........ *G01N 33/007* (2013.01); *G01M 15/102* (2013.01); *G01N 1/2252* (2013.01); *G01N 21/274* (2013.01); *G01N 21/3504* (2013.01); *G01N 33/0006* (2013.01); *G01N 33/0016* (2013.01); *G01N 33/004* (2013.01); *G01N 2033/0072* (2013.01)

(58) Field of Classification Search
CPC ............... G01N 33/007; G01N 21/274; G01N 33/0006; G01N 33/0016; G01N 21/3504; G01N 1/2252; G01N 33/004; G01N 2033/0072; G01M 15/102; G01M 15/104; G01M 15/108
USPC ......... 73/1.03, 1.06, 1.07, 23.1, 23.32, 1.58, 73/1.66, 1.68
See application file for complete search history.

(56) References Cited

U.S. PATENT DOCUMENTS

| | | | | |
|---|---|---|---|---|
| 5,239,492 | A | * 8/1993 | Hartwig ............. | G01N 33/0006 702/27 |
| 2006/0236752 | A1 | 10/2006 | Nakamura | |

(Continued)

FOREIGN PATENT DOCUMENTS

JP 2004-117261 A 4/2004

OTHER PUBLICATIONS

EESR dated Aug. 8, 2019 dated for European Patent Application No. 18 204 516.1, 8 pgs.

*Primary Examiner* — Robert R Raevis
(74) *Attorney, Agent, or Firm* — Brooks Kushman P.C.

(57) ABSTRACT

The present invention includes: connecting a pressure varying device to a sample gas introduction port and a gas discharge port of a gas analysis apparatus; depressurizing or pressurizing the sample gas introduction port and the gas discharge port by the pressure varying device; introducing calibration gas from a calibration gas introduction port of the gas analysis apparatus in a depressurized or pressurized state; and calculating a pressure correction factor for the gas analysis apparatus with use of a measurement result of the calibration gas by the gas analysis apparatus.

14 Claims, 5 Drawing Sheets

(56) References Cited

U.S. PATENT DOCUMENTS

2016/0077072 A1* 3/2016 Tsuzuki ............ G01N 33/0006
73/1.06
2017/0299459 A1 10/2017 Spartz
2017/0299505 A1 10/2017 Nishimura

* cited by examiner

CALIBRATION METHOD FOR GAS ANALYSIS APPARATUS, GAS ANALYSIS SYSTEM, AND PRESSURE VARYING DEVICE

CROSS-REFERENCE TO RELATED APPLICATION

This application claims priority to Japanese Application No. 2017-214121, filed Nov. 6, 2017, the disclosure of which is incorporated in its entirety by reference herein.

TECHNICAL FIELD

The embodiments of the present invention relate to a calibration method for a gas analysis apparatus, a gas analysis system, and a pressure varying device.

BACKGROUND ART

In recent years, for component analysis of exhaust gas discharged from a vehicle running on a road and for a vehicle test, an exhaust gas analysis apparatus of a vehicle-mounted type has been used. This exhaust gas analysis apparatus includes analyzers for analyzing components such as nitrogen oxides ($NO_x$), carbon monoxide (CO), and carbon dioxide ($CO_2$).

In each of the analyzers provided in the exhaust gas analysis apparatus, a measured value is subjected to pressure effect due to pressure variation caused by a variation in altitude during an on-road run. For this reason, the exhaust gas analysis apparatus makes a pressure correction to a measured value by each analyzer using a pressure correction factor for correcting for the pressure effect, and thereby calculates the concentration of each component normalized with reference pressure (e.g., pressure at the time of calibration curve preparation).

In addition, a pressure correction factor used for the exhaust gas analysis apparatus is a common one prepared in accordance with the following procedure.

Specifically, several exhaust gas analysis apparatuses are carried into a depressurization/pressurization test chamber, and calibration gas whose concentration is known is measured by the several exhaust gas analysis apparatuses under reduced/increased pressure. Then, from the relationship between the average value of multiple measured values obtained by the several exhaust gas analysis apparatuses and pressure at the time of the calibration gas measurement, the pressure correction factor is obtained. The pressure correction factor obtained in this manner is used as pressure correction factors for multiple exhaust gas analysis apparatuses.

However, there are variations in pressure variation characteristics among exhaust gas analysis apparatuses, and therefore the use of the common pressure correction factor may result in an exhaust gas analysis apparatus whose correction accuracy is low. On the other hand, in order to ensure the correction accuracy, it is necessary to employ a pressure correction factor specific to each exhaust gas analysis apparatus. For this purpose, the above-described depressurization/pressurization test chamber has to be used, which simultaneously requires large-scale work of carrying an exhaust gas analysis apparatus into the depressurization/pressurization test chamber. In addition, a manufacturer or a user who has no depressurization/pressurization test chamber has to borrow or purchase a depressurization/pressurization test chamber, causing low productivity.

CITATION LIST

Patent Literatures

Patent Literature 1: Japanese Unexamined Patent Application Publication No. 2004-117261

SUMMARY

Technical Problem

Therefore, an embodiment of the present invention has been made in order to solve the above-described problems, and a main object thereof is to make it possible to obtain a pressure correction factor for each exhaust gas analysis apparatus without using a depressurization/pressurization test chamber.

Solution to Problem

That is, a calibration method for a gas analysis apparatus according to one aspect of the present invention includes: connecting a pressure varying device to a sample gas introduction port and a gas discharge port of the gas analysis apparatus; depressurizing or pressurizing the sample gas introduction port and the gas discharge port by the pressure varying device; introducing calibration gas from a calibration gas introduction port of the gas analysis apparatus in a depressurized or pressurized state; and calculating a pressure correction factor for the gas analysis apparatus with use of a measurement result of the calibration gas by the gas analysis apparatus.

According to one aspect of the present invention, since the pressure varying device is connected to the sample gas introduction port and the gas discharge port of the gas analysis apparatus, the gas analysis apparatus can reproduce the depressurized or pressurized state without using a pressurization/depressurization test chamber. Accordingly, a pressure correction factor can be calculated individually for each of multiple gas analysis apparatuses by a low-cost and simplified method. As a result, as compared with a conventional gas analysis apparatus using a common pressure correction factor, the accuracy of pressure correction can be improved. Also, a pressure correction factor can be easily updated for each shipped exhaust gas analysis apparatus at a shipping destination or the like.

In order to accurately obtain the pressure correction factor, it is desirable to include: depressurizing or pressurizing to multiple pressures by the pressure varying device; and calculating the pressure correction factor for the gas analysis apparatus so that a measurement result of the calibration gas at each of the multiple pressures becomes equal to a measurement result of the calibration gas at reference pressure. In addition, the reference pressure may be pressure at the time of preparing a calibration curve for the gas analysis apparatus or pressure at the time of zero/span calibration.

It is desirable to include: introducing an excessive amount of the calibration gas from the calibration gas introduction port; and measuring the calibration gas while making the calibration gas overflow from the sample gas introduction port. Such a configuration makes it possible to introduce the calibration gas into an analyzer of the gas analysis apparatus without dilution.

It is desirable that the calibration method of one embodiment of the present invention includes: introducing calibration gases for respective multiple measurement target components; and calculating pressure correction factors for the respective multiple measurement target components. In this case, it is desirable to include: mixing and introducing the calibration gases for the respective multiple measurement target components; and calculating the pressure correction factors for the respective multiple measurement target components.

As a conventional gas analysis apparatus, there is one further including an atmosphere introduction port. The atmosphere introduced from the atmosphere introduction port may be used for gas dilution or ozone generation. In addition, ozone generated from the atmosphere is used for measurement by an analyzer. The analyzer in this case may be a nitrogen oxide meter based on a chemiluminescence (CLD) method using the oxidation reaction of ozone gas.

Even in such a case, a measurement result by the gas analysis apparatus may be subjected to pressure effect due to pressure variation via the atmosphere introduction port. Therefore, it is desirable that the calibration method for the gas analysis apparatus of one embodiment of the present invention includes: connecting the pressure varying device to the atmosphere introduction port; and depressurizing or pressurizing the sample gas introduction port and the gas discharge port.

When the gas analysis apparatus is one of a vehicle-mounted type, the effect of one embodiment of the present invention can be markedly produced because atmospheric pressure easily varies due to a running route during a running test on an actual road.

Also, a pressure correction method for a gas analysis apparatus according to one embodiment of the present invention includes: with use of the pressure correction factor obtained by the calibration method described above, correcting a measurement result of actual measurement by the gas analysis apparatus to a measurement result at reference pressure for the gas analysis apparatus on the basis of pressure at time of the actual measurement.

Further, an inspection method for a gas analysis apparatus according to one embodiment of the present invention includes: connecting a pressure varying device to a sample gas introduction port and a gas discharge port of the gas analysis apparatus having a pressure correction function using a pressure correction factor; depressurizing or pressurizing the sample gas introduction port and the gas discharge port by the pressure varying device; introducing calibration gas from a calibration gas introduction port of the gas analysis apparatus in a depressurized or pressurized state; and comparing a measured value after correction using the pressure correction factor for the gas analysis apparatus and known concentration of the calibration gas at reference pressure.

In addition, a pressure varying device according to one embodiment of the present invention is one used when obtaining a pressure correction factor for a gas analysis apparatus, and includes: a first flow path whose one end is to be connected to a sample gas introduction port of the gas analysis apparatus; a second flow path whose one end is to be connected to a gas discharge port of the gas analysis apparatus; and a pump for depressurizing or pressurizing the sample gas introduction port and the gas discharge port via the first flow path and the second flow path.

In order to depressurize or pressurize the gas analysis apparatus by a common pump, it is desirable that the first flow path and the second flow path are connected to the pump via a merged flow path. In order to reduce the pulsation of the pump, it is desirable that the merged flow path comprises a buffer tank, and the other ends of the first flow path and the second flow path are connected to the pump via the buffer tank.

When regulating pressure by a pump, it is difficult to regulate the pressure because of the effect of the pulsation of the pump or the like. In order to solve this problem to easily regulate the pressures in the respective flow paths, it is desirable to further include: an atmosphere introduction path for introducing the atmosphere into the merged flow path; and in the atmosphere introduction path, a pressure regulation part that regulates the pressures in the first flow path and the second flow path As described above, as a gas analysis apparatus, there is one having an atmosphere introduction port. In this case, it is desirable that the pressure varying device further includes a third flow path whose one end is to be connected to an atmosphere introduction port of the gas analysis apparatus, and the pump is one that depressurizes or pressurizes the atmosphere introduction port via the third flow path.

Also, in order to introduce the atmosphere into the atmosphere introduction port of the gas analysis apparatus, it is desirable that the atmosphere is introduced into the third flow path. Specifically, it is desirable that the atmosphere introduction path is connected to the buffer tank, and the other end of the third flow path is connected to the atmosphere introduction path.

Further, a gas analysis system according to one embodiment of the present invention includes: a gas analysis apparatus that analyzes a measurement target component in sample gas; and the above-described pressure varying device.

Advantageous Effects

According to embodiments of the present invention described above, since the pressure varying device is connected to the sample gas introduction port and the gas discharge port of the gas analysis apparatus, a pressure correction factor can be obtained for each exhaust gas analysis apparatus without using a depressurization/pressurization test chamber.

DESCRIPTION OF EMBODIMENTS

In the following, an exhaust gas analysis system 100 according to one embodiment of the present invention will be described with reference to the drawings.

Figure 1:
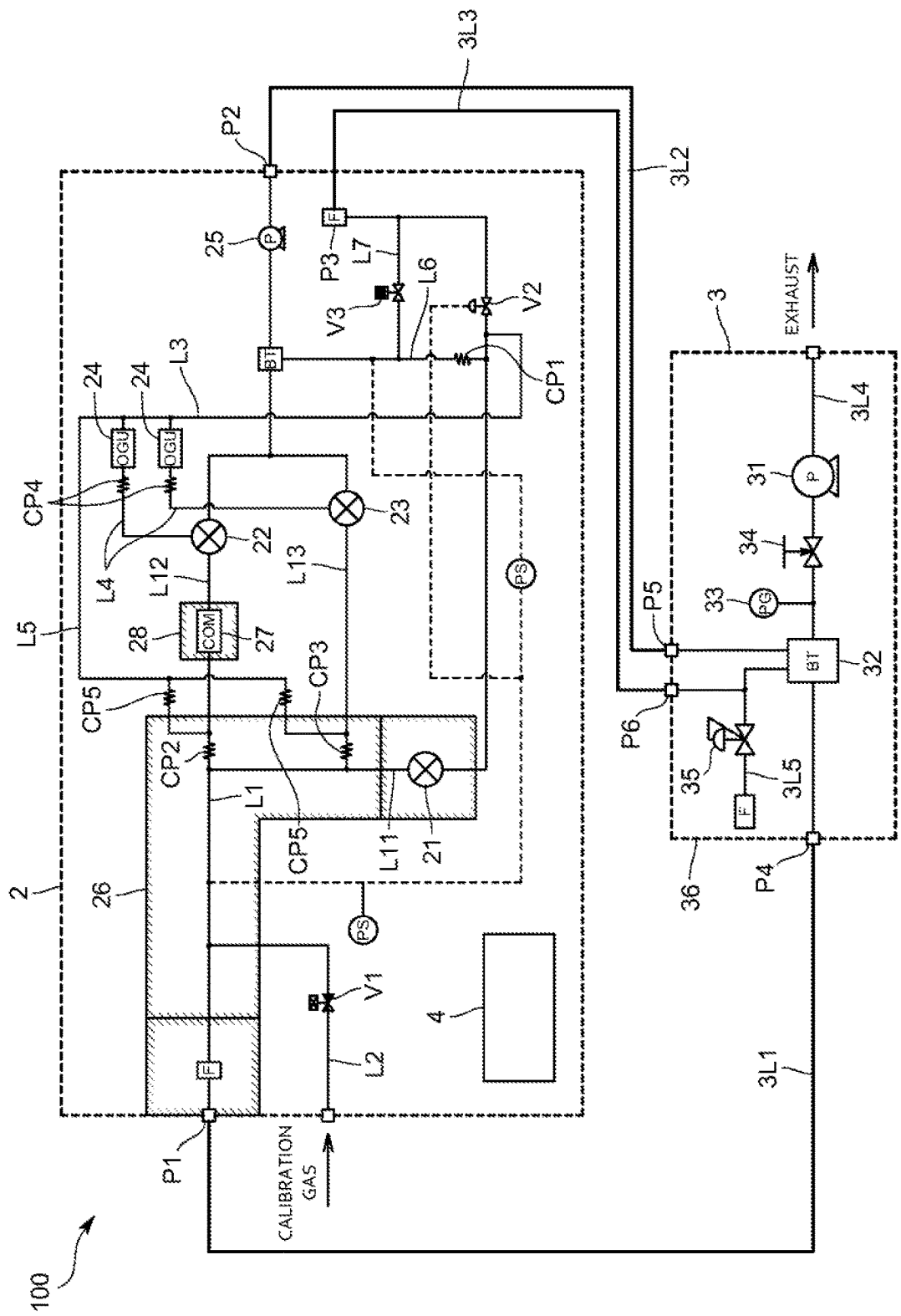
FIG. 1 is an overall schematic diagram of an exhaust gas analysis system according to one embodiment of the present invention.

As illustrated in FIG. 1, the exhaust gas analysis system 100 of the present embodiment includes: a vehicle-mounted exhaust gas analysis apparatus 2 to be mounted in a vehicle; and a pressure varying correcting device 3 that is connected to the exhaust gas analysis apparatus 2 and used when obtaining a pressure correction factor for the exhaust gas analysis apparatus 2.

In addition, although not illustrated, the exhaust gas analysis system 100 includes: an exhaust gas sampling mechanism including a sampling pipe for sampling the whole or part of exhaust gas discharged through an exhaust pipe connected to an internal combustion engine (engine) of a vehicle, and the like; a heating pipe for introducing the exhaust gas sampled by the exhaust gas sampling mechanism into the exhaust gas analysis apparatus 2 while heating the sampled exhaust to a predetermined temperature or keeping the temperature of the sampled exhaust gas; and a power supply for supplying electric power to the exhaust gas analysis apparatus 2 and the heating pipe.

<Exhaust Gas Analysis Apparatus 2>

The exhaust gas analysis apparatus 2 is one that analyzes measurement target components in the exhaust gas, such as carbon monoxide (CO), carbon dioxide ($CO_2$), nitrogen oxides ($NO_x$), methane ($CH_4$), and total hydrocarbons (THC), and in the present embodiment, includes a $CO/CO_2$ analyzer 21, an $NO_x$ analyzer 22, and an NO analyzer 23.

The $CO/CO_2$ analyzer 21 is one that continuously measures the concentration of carbon monoxide or carbon dioxide contained in the exhaust gas by a non-dispersive infrared absorption (NDIR) method. The $NO_x$ analyzer 22 is one that continuously measures the concentration of NOx in the exhaust gas by a chemiluminescence (CLD) method. The NO analyzer 23 is also one that continuously measures the concentration of NO in the exhaust gas by the CLD method as with the NOx analyzer 22. In addition, the exhaust gas analysis apparatus 2 can be provided with various analyzers depending on a measurement target component. For example, when measuring methane ($CH_4$) or total hydrocarbons (THC), the exhaust gas analysis apparatus 2 includes an analyzer using a hydrogen flame ionization (FID) method. Further, pieces of analysis data obtained by the analyzers 21 to 23 are outputted to an information processing unit 4, and the information processing unit 4 processes, and records or displays the pieces of analysis data. In addition, the multiple analyzers described above may be respectively provided as separate bodies.

The information processing unit 4 is a dedicated or general-purpose computer having a CPU, an internal memory, an AD converter, an input/output inverter, and the like, and acquires not only the pieces of analysis data from the analyzers 21 to 23, but pieces of data from another sensor group to process, and record or display them. In addition, the sensor group includes: an air-fuel ratio sensor for measuring the air-fuel ratio (A/F) of the vehicle, a flowmeter for measuring the flow rate of the exhaust gas discharged through the exhaust pipe, a GPS sensor for detecting the position of the vehicle, a temperature sensor for measuring the temperature outside the vehicle, a humidity sensor for measuring the humidity outside the vehicle, a pressure sensor for measuring the pressure (atmospheric pressure) outside the vehicle, and the like.

Further, the exhaust gas analysis apparatus 2 is provided with: a sample gas introduction port P1 for introducing the exhaust gas into the $CO/CO_2$ analyzer 21, the $NO_x$ analyzer 22, and the NO analyzer 23; and a gas discharge port P2 for discharging the exhaust gas and the like having passed through the analyzers 21 to 23. Still further, the exhaust gas analysis apparatus 2 is provided with: ozone generators 24 for generating ozone gases to be used for the $NO_x$ analyzer 22 and the NO analyzer 23; and an atmosphere introduction port P3 for introducing the atmosphere into the ozone generators 24. That is, in the present embodiment, ports opened to the atmosphere and affected by pressure variation are the sample gas introduction port P1, the gas discharge port P2, and the atmosphere introduction port P3.

The sample gas introduction port P1 is connected to an upstream end of a main flow path L1 through which the exhaust gas flows, and in the main flow path L1, the $CO/CO_2$ analyzer 21, the $NO_x$ analyzer 22, and the NO analyzer 23 are provided. Also, a downstream end of the main flow path L1 is connected with the gas discharge port P2.

Further, in the main flow path L1, a suction pump 25 is provided downstream of the $CO/CO_2$ analyzer 21, the $NO_x$ analyzer 22, and the NO analyzer 23. The suction pump 25 allows the exhaust gas sampling mechanism to sample the exhaust gas, as well as allows the exhaust gas to be introduced from the sample gas introduction port P1 into the main flow path L1 and measured by the respective analyzers 21 to 23. In addition, the suction pump 25 allows the $CO/CO_2$ analyzer 21, the $NO_x$ analyzer 22, and the NO analyzer 23 to perform analysis under a reduced pressure condition.

The main flow path L1 in the present embodiment is configured to branch into flow paths L11 to L13 corresponding to the respective analyzers 21 to 23, and to be connected with the respective analyzers 21 to 23 in parallel, and the flow paths L11 to L13 merge together on the upstream side of the suction pump 25. The respective branch paths L11 to L13 are provided with constant flow rate devices CP1 to CP3 for making constant the flow rate of the exhaust gas flowing into the respective analyzers 21 to 23, such as capillaries. In addition, in the main flow path L1, a flow path from the sample gas introduction port P1 to the $CO/CO_2$ analyzer 21 and the $CO/CO_2$ analyzer 21 are heated to a predetermined temperature (e.g., 95° C.) by a heating block 26 so as to prevent moisture from condensing. Also, a converter catalyst 27 for converting $NO_x$ to NO is provided upstream of the $NO_x$ analyzer 22 in the branch path L12 provided with the $NO_x$ analyzer 22, and the converter catalyst 27 is heated to a predetermined temperature (e.g., 210° C.) by a heating block 28.

On the upstream side of the respective analyzers 21 to 23 in the main flow path L1 (on the upstream side of the branch point), a calibration gas flow path L2 for introducing calibration gas whose concentration is known is connected. The calibration gas flow path L2 is connected to a calibration gas cylinder (not illustrated). Also, the calibration gas flow path L2 is provided with an electromagnetic on-off valve V1 for switching supply/stop of the calibration gas to the main flow path L1. In addition, the electromagnetic on-off valve V1 is controlled by a valve control part of the information processing unit 4.

The atmosphere introduction port P3 is connected with the upstream end of an atmosphere introduction flow path L3, and a downstream end of the atmosphere introduction flow path L3 is connected to the ozone generators 24. The ozone gases generated by the ozone generators 24 are introduced into the $NO_x$ analyzer 22 and the NO analyzer 23 through ozone gas flow paths L4 respectively connecting between one ozone gas generator 24 and the $NO_x$ analyzer 22 and between the other ozone gas generator 24 and the NO analyzer 23.

Figure 2:
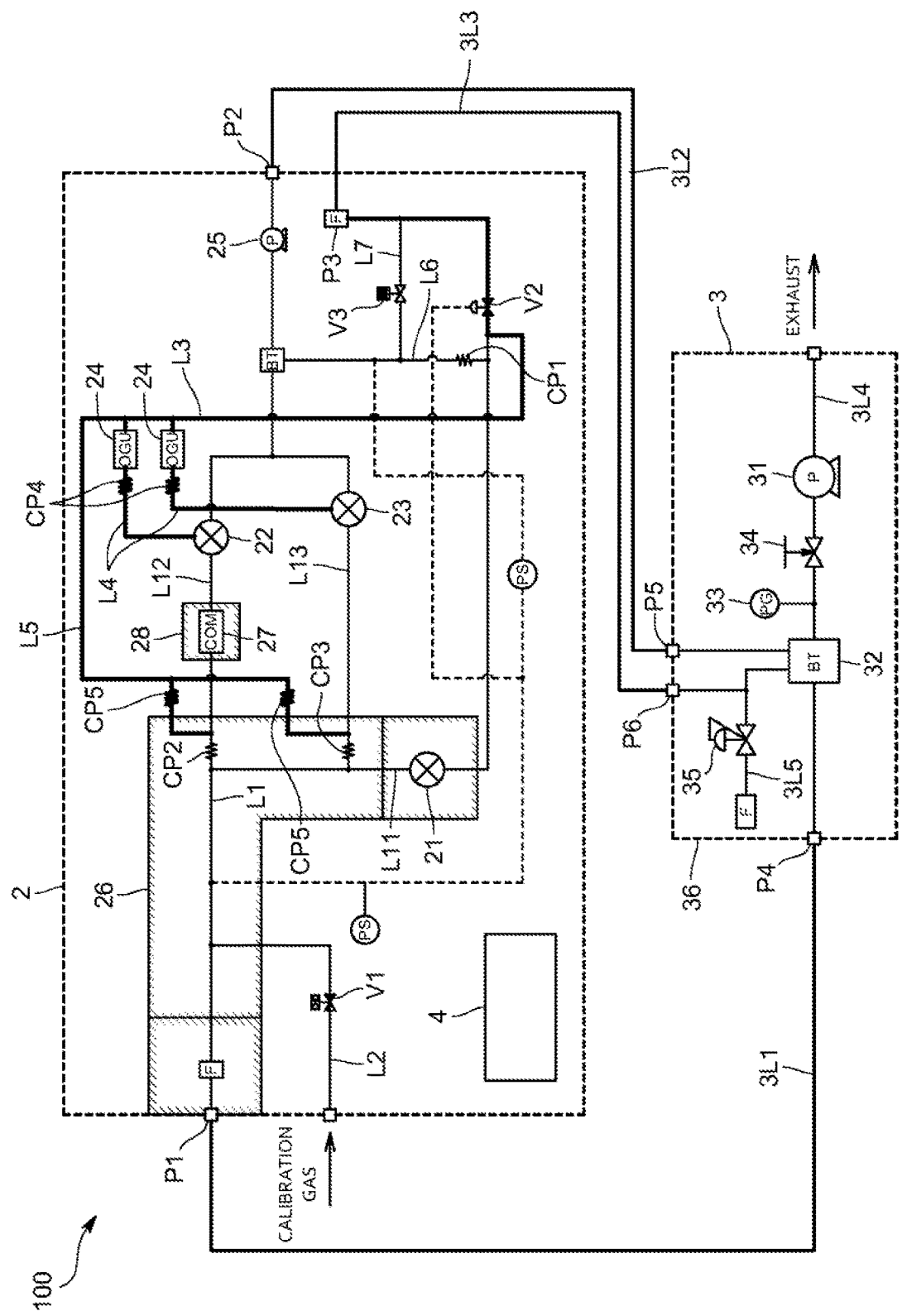
FIG. 2 is a schematic diagram illustrating the flow of the atmosphere from an atmosphere introduction port of the exhaust gas analysis system according to the same embodiment.

In addition, as illustrated in FIG. 2, the ozone gas flow paths L4 are respectively provided with constant flow rate devices CP4 for making the flow rates of the ozone gases constant, such as capillaries. Also, on the downstream side of the heating block 26 in the main flow path L1 and on the upstream side of the $NO_x$ analyzer 22 and the NO analyzer 23, the atmosphere introduction flow path L3 is connected with a branch flow path L5 for introducing the atmosphere to dilute the exhaust gas. The branch flow path L5 is provided with a constant flow rate device CP5 for making the flow rate of the atmosphere constant, such as a capillary. The pressures of the ozone generators 24 are regulated to a predetermined pressure by a pressure regulation valve V2 so as to be a first pressure (e.g., −20 kPa) with respect to the pressure at the atmosphere introduction port P3, and the pressures of the analyzers 22 and 23 are regulated to a predetermined pressure by the pressure regulation valve V2 and the constant flow rate devices CP4 so as to be a second pressure (e.g., −40 kPa) with respect to the pressure at the atmosphere introduction port P3. Further, pressures on the downstream sides of the constant flow rate devices CP2 and CP3 (analyzers 22 and 23) are regulated to a predetermined pressure by the pressure regulation valve V2 and the constant flow rate device CP5 so as to be the second pressure (e.g., −40 kPa) with respect to the pressure at the atmosphere introduction port P3. In this manner, constant flow rates of the ozone gases are supplied to the analyzers 22 and 23, and a constant flow rate of the dilution air is supplied to the main flow path L1.

Figure 3:
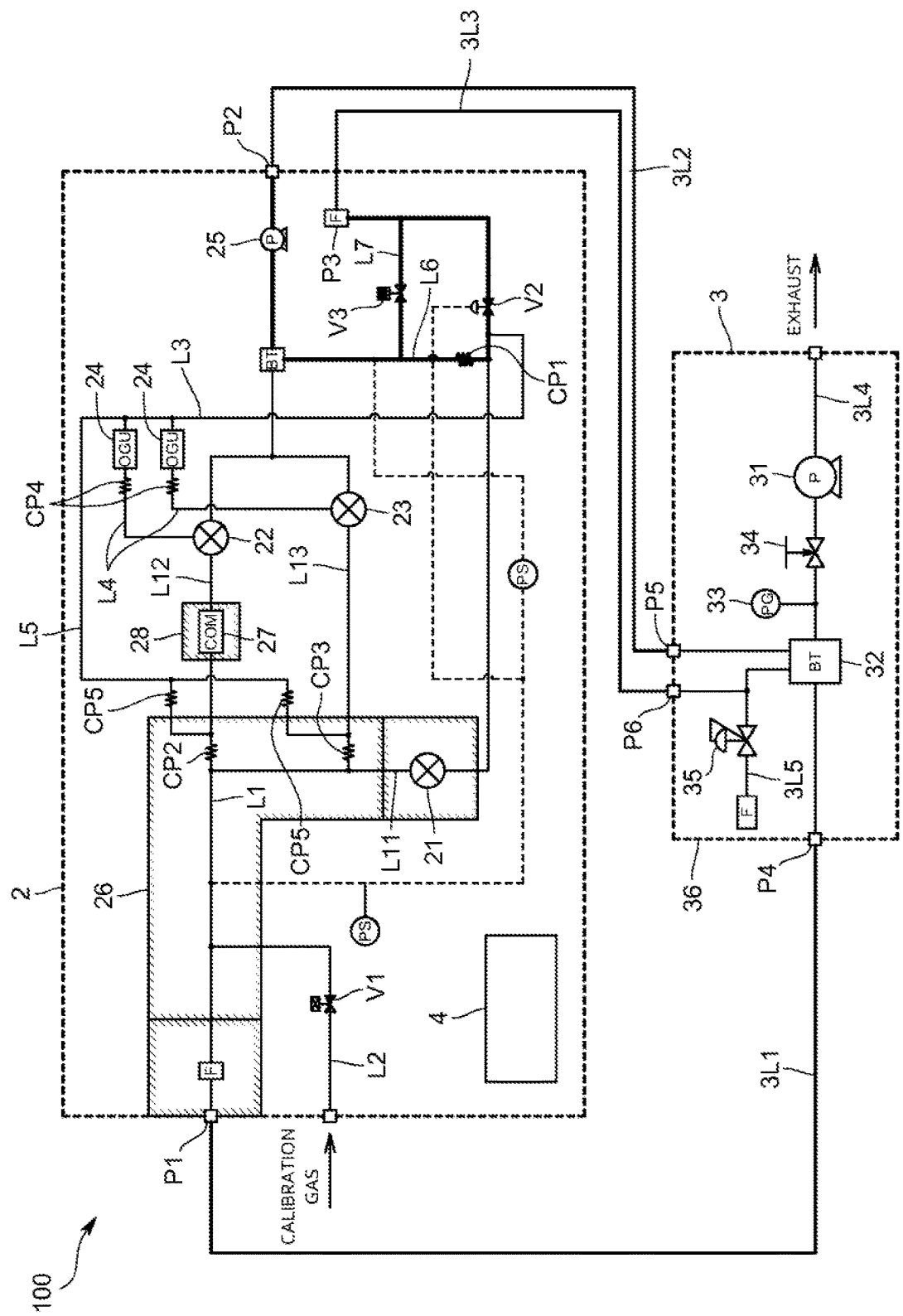
FIG. 3 is a schematic diagram illustrating the flow of the atmosphere from the atmosphere introduction port of the exhaust gas analysis system according to the same embodiment.

In addition, as illustrated in FIG. 3, the atmosphere introduction flow path L3 also carries a constant flow rate function for flowing a constant flow rate of the exhaust gas to the $NO_x$ analyzer 22 and the NO analyzer 23. Specifically, the atmosphere introduction flow path L3 is connected with a connection flow path L6 that is connected to the downstream side of the $NO_x$ the analyzer 22 and the NO analyzer 23 in the main flow path L1 and to the upstream side of the suction pump 25. The connection flow path L6 in the present embodiment is a flow path common to a part of the branch flow path L11. Also, the upstream side of the connection point of the connection flow path L6 in the atmosphere introduction flow path L3 (on the upstream side of the constant flow rate device CP1), a pressure regulation valve V2 is provided, and a bypass flow path L7 connecting between the connection flow path L6 and the atmosphere introduction flow path L3 is provided with an electromagnetic proportional valve V3. The pressure regulation valve V2 is one that refers to input pressure on the upstream side of the constant flow rate device CP2 in the main flow path L1, and regulates pressure on the downstream side of the pressure regulation valve V2 to a predetermined pressure so as to be the first pressure (e.g., −20 kPa) with respect to the input pressure. Also, the electromagnetic proportional valve V3 is one that refers to the input pressure on the upstream side of the constant flow rate device CP2 in the main flow path L1 and output pressure on the downstream side of the electromagnetic proportional valve V3 in the connection flow path L6, and regulates the output pressure on the downstream side of the electromagnetic proportional valve V3 (the pressure of a buffer tank BT) to a predetermined pressure so as to be the second pressure (e.g., −40 kPa) with respect to the input pressure. That is, the pressure of the buffer tank BT is reduced to the predetermined pressure by the pressure regulation valve V2 and the constant flow rate device CP1 so as to be the second pressure (e.g., −40 kPa) with respect to the pressure at the atmosphere introduction port P3. As described above, the pressure regulation valve V2 and the electromagnetic proportional valve V3 makes constant (−20 kPa) the differential pressures between the upstream side pressure and the downstream side pressure of the constant flow rate devices CP1 to CP3 provided in the respective branch paths L11 to L13, and therefore a constant flow rate of the exhaust gas can be flowed to the $CO/CO_2$ analyzer 21, the $NO_x$ analyzer 222, and the NO analyzer 23. In addition, the pressure regulation valve V2 and the electromagnetic proportional valve V3 only have to be configured so that any one of them is provided. Further, the pressure regulation valve V2 may be replaced with an electromagnetic proportional valve.

<Pressure Varying Device 3>

The pressure varying device 3 is used when calibrating the above-described exhaust gas analysis apparatus 2, and specifically, used when obtaining pressure correction factors for the exhaust gas analysis apparatus 2. In addition, the pressure correction factors in the present embodiment are a factor for correcting a pressure-dependent variation in CO concentration or $CO_2$ concentration obtained by the $CO/CO_2$ analyzer 21, a factor for correcting a pressure-dependent variation in $NO_x$ concentration obtained by the $NO_x$ analyzer 22, and a factor for correcting a pressure-dependent variation in NO concentration obtained by the NO analyzer 23. Specifically, the pressure correction factors are ones for normalizing the concentrations with reference pressure (in the present embodiment, pressure at the time of calibration curve preparation).

The pressure varying device 3 is one that depressurizes the multiple ports P1 to P3 of the exhaust gas analysis apparatus 2, which are opened to the atmosphere. Specifically, the pressure varying device 3 includes: a first flow path 3L1 whose one end is connected to the sample gas introduction port P1; a second flow path 3L2 whose one end is connected to the gas discharge port P2 of the exhaust gas analysis apparatus 2; a third flow path 3L3 whose one end is connected to the atmosphere introduction port P3 of the exhaust gas analysis apparatus 2; and a suction pump 31 for depressurizing the sample gas introduction port P1, the gas discharge port P2, and the atmosphere introduction port P3 via the flow paths 3L1 to 3L3.

The other ends of the first flow path 3L1 and second flow path 3L2 are connected to the buffer tank 32. The buffer tank 32 is connected to the suction pump 31 via an exhaust flow path 3L4. The exhaust flow path 3L4 is provided with a gauge pressure sensor 33, and a flow rate regulation part 34 such as a needle valve. The flow rate regulation part 34 regulates an exhaust flow rate by the suction pump 31.

Also, the buffer tank 32 is connected with an atmosphere introduction path 3L5 for introducing the atmosphere. In addition, the atmosphere introduction path 3L5 is connected with the other end of the third flow path 3L3. In the atmosphere introduction path 3L5, a pressure regulation part 35 such as a pressure regulation valve is provided on the upstream side of the connection point of the third flow path 3L3. The pressure regulation part 35 regulates the pressures in the first flow path 3L1, the second flow path 3L2, and the third flow path 3L3 to be constant.

Further, the suction pump 31, the buffer tank 32, the gauge pressure sensor 33, and the pressure regulation parts 34 and 35 of the pressure varying device 3 of the present embodiment are contained in a housing 36. In addition, connection ports P4 to P6 provided on the housing 36 are respectively connected with connecting pipes constituting parts of the first flow path 3L1, the second flow path 3L2, and the third flow path 3L3. By connecting the housing 36 and the exhaust gas analysis apparatus 2 via the connecting pipes as described above, the connection between the exhaust gas analysis apparatus 2 and the pressure varying device 3 can be facilitated.

In this configuration, when the suction pump 25 of the exhaust gas analysis apparatus 2 and the suction pump 31 of the pressure varying device 3 perform suction operation to supply the calibration gas through the calibration gas flow path L2, the flow of the gas is as follows.

That is, the calibration gas is sucked from the sample gas introduction port P1 and the gas discharge port P2 through the first flow path 3L1 and the second flow path 3L2. Also, the atmosphere is introduced into the atmosphere introduction port P3 of the exhaust gas analysis apparatus 2 through the third flow path 3L3 via the atmosphere introduction path 3L5. Since the third flow path 3L3 is connected to the atmosphere introduction path 3L5, the calibration gas flowing into the buffer tank 32 through the first flow path 3L1 and the second flow path 3L2 does not have a possibility of flowing into the third flow path 3L3. This allows the calibration gas to be supplied to the respective analyzers 21 to 23 in a state where the sample gas introduction port P1, the gas discharge port P2, and the atmosphere introduction port P3 are depressurized.

<Calibration Method (Pressure Correction Factor Calculation Method)>

Figure 4:
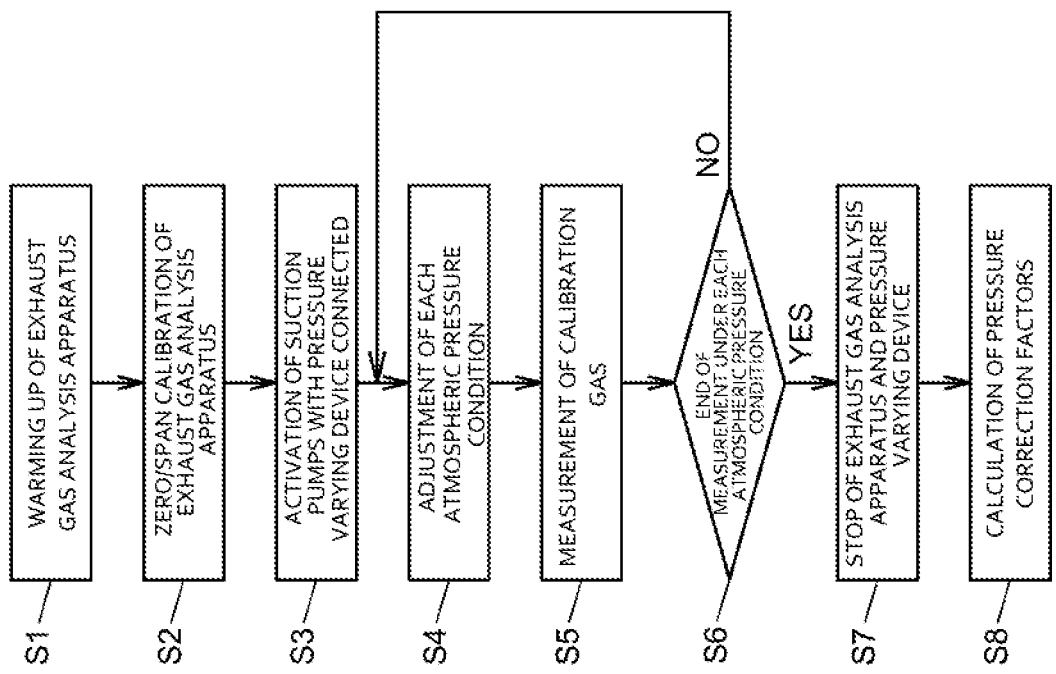
FIG. 4 is a flowchart of a calibration method of the same embodiment.

Next, a pressure correction factor calculation method using the pressure varying device 3 configured as described above will be described with reference to FIG. 4. The calibration method of the present embodiment includes, in addition to the zero/span calibration of the exhaust gas analysis apparatus 2, calculating the pressure correction factors for the exhaust gas analysis apparatus 2. In addition, the calibration method may include preparing a calibration curve.

First, the exhaust gas analysis apparatus 2 as a calibration target is prepared. At this time, when the exhaust gas analysis apparatus 2 is one mounted in a vehicle, the exhaust gas analysis apparatus 2 may be in a state of being mounted or in a state of being dismounted from the vehicle.

Then, the exhaust gas analysis apparatus 2 is warmed up (Step S1). In addition, when the exhaust gas analysis apparatus 2 has a pressure correction function, the pressure correction function is turned off.

After the warming up, a calibration gas for zero calibration is flowed into the exhaust gas analysis apparatus 2 to perform zero calibration in an atmospheric pressure environment. Also, a calibration gas for span calibration is flowed into the exhaust gas analysis apparatus 2 to perform span calibration (Step S2). These calibration gases are supplied through the calibration gas flow path L2. In addition, the pressure varying device 3 is in a stopped state.

After that, the respective flow paths 3L1 to 3L3 of the pressure varying device 3 are connected to the respective ports P1 to P3 of the exhaust gas analysis apparatus 2. In this state, the suction pump 25 of the exhaust gas analysis apparatus 2 and the suction pump 31 of the pressure varying device 3 are activated (Step S3).

Then, the pressure (the pressure of the gauge pressure sensor 33) in the buffer tank 32 is regulated to be constant (an atmospheric pressure condition at 0 m to 2500 m) by the pressure regulation part 35 of the pressure varying device 3 (Step S4). As the order of changing the atmospheric pressure condition, it is conceivable to change the atmospheric pressure in such a manner as to gradually increase the altitude to the predetermined maximum altitude and then gradually decrease the altitude, like, for example, 0 m, 500 m, 1000 m, 1500 m, 2000 m, 2500 m, 2000 m, 1000 m, and 0 m. At this time, the pressure in the buffer tank 32 is controlled to a desired pressure by operating the pressure regulation part 35 on the basis of a measured value by the gauge pressure sensor 33 of the pressure varying device 3. This operation may be automatically controlled using a computer or manually performed by an operator.

Under each atmospheric pressure condition, the calibration gas for zero calibration and the calibration gas for span calibration are flowed to perform measurement by each of the analyzers 21 to 23 (Step S5). These calibration gases are flowed into the main flow path L1 through the calibration gas flow path L2. At this time, an excessive amount of each calibration gas is supplied so as to not only flow toward the downstream side of the connecting point (toward the gas discharge port P2) but also flow toward the upstream side (toward the sample gas introduction port P1). That is, the calibration gas flows out from the sample gas introduction port P1 to the first flow path 3L1. This allows the pure calibration gas to be flowed into the respective analyzers 21 to 23. This is because when the calibration gas does not flow back from the sample gas introduction port P1, the atmosphere is introduced from the sample gas introduction port P1, and the calibration gas is diluted, thus failing to perform accurate calibration. In addition, the excessive amount means that the supply flow rate of the calibration gas is larger than a flow rate obtained by subtracting an introduction amount from the atmosphere introduction port P3 from a discharge amount from the gas discharge port P2.

After the end of the measurement under the respective atmospheric pressure conditions (Step S6), the pressure varying device 3 and the exhaust gas analysis apparatus 2 are stopped (Step S7). Then, from measurement results obtained by the measurement under the respective atmospheric pressure conditions, the pressure correction factors are calculated (Step S8). Specifically, the pressure correction factors are prepared such that the measurement results obtained by the measurement under the respective atmospheric pressure conditions become equal to the measured values of the calibration gas at the reference pressure.

The pressure correction factors for the respective analyzers 21 to 23 can be obtained by, while variously changing the pressure, acquiring measured values by the respective analyzers 21 to 23 at each pressure.

Note that the pressure correction factors may be configured to be calculated by the information processing unit 4 or manually calculated by an operator. In addition, the pressure correction factors may be represented in a tabular format or a functional format. Data on the pressure correction factors obtained in this manner is stored in the internal memory of the information processing unit 4.

By performing the above processing for each of calibration gases having different concentrations, the pressure correction factors at each concentration can be obtained. In addition, when using multiple calibration gases of different gas species, the same operation may be performed for each of the calibration gases or calibration may be performed using mixed gas of the multiple calibration gases.

By using the pressure correction factors, the information processing unit 4 corrects for the pressure difference from the reference pressure (pressure at the time of calibration curve preparation) to calculate concentrations normalized with the pressure at the time of calibration curve preparation from pressure obtained by a pressure sensor (not illustrated) during an actual run on a road and concentrations obtained by the respective analyzers 21 to 23.

Figure 5:
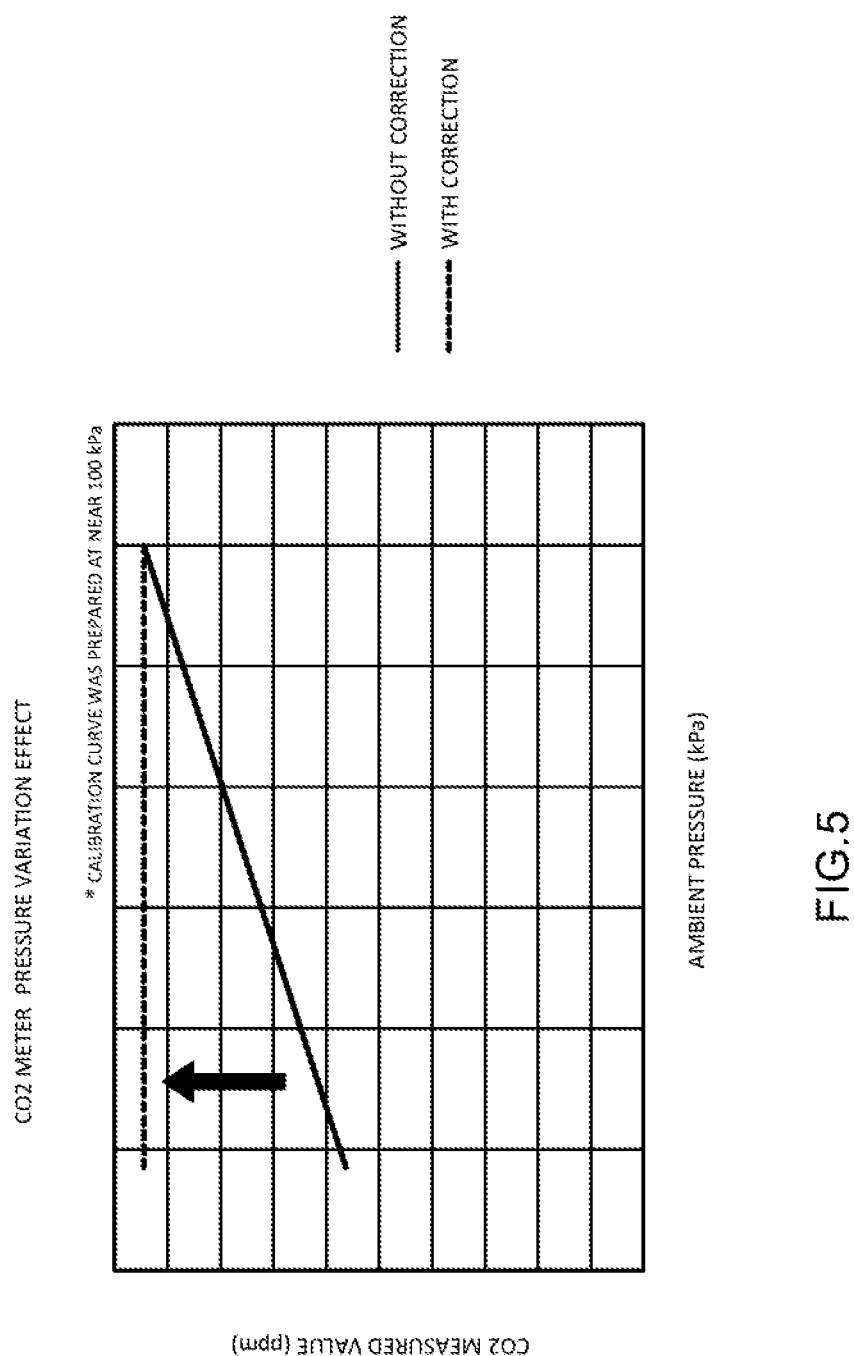
FIG. 5 is a diagram illustrating the effect of pressure variation on $CO_2$ concentration and corrected concentration in the same embodiment.

FIG. 5 illustrates the effect of pressure variation on $CO_2$ concentration and corrected concentration. This example shows the result of measuring the $CO_2$ concentration using a $CO_2$ meter for which a calibration curve was prepared at near 100 kPa. It turns out that a measured value by the $CO_2$ meter gradually decreases as ambient pressure decreases from 100 kPa. On the other hand, by using the pressure correction factor in the present embodiment, regardless of a variation in ambient pressure, the measured value by the $CO_2$ meter is corrected to a measured value at 100 kPa at which a calibration curve was prepared. In addition, the effect of pressure variation is different depending on the measurement principle of an analyzer, and a measured value may increase as pressure decreases.

<Effects of Present Embodiment>

In the gas analysis system 100 of the present embodiment, since the suction pump 31 is connected to the sample gas introduction port P1 and gas discharge port P2 of the exhaust gas analysis apparatus 2, the exhaust gas analysis apparatus 2 can reproduce a depressurized state without using a depressurization test chamber. Accordingly, correction factors can be calculated individually for each of multiple exhaust gas analysis apparatuses 2 by a low-cost and simplified method. As a result, as compared with a conventional exhaust gas analysis apparatus 2 using common pressure correction factors, the accuracy of pressure correction can be improved. Also, pressure correction factors can be easily updated for each shipped exhaust gas analysis apparatus 2 at a shipping destination or the like.

Note that the present invention is not limited to the above-described embodiment.

For example, the exhaust gas analysis apparatus 2 is one that has a function of diluting the exhaust gas and the ozone generators, and therefore has the atmosphere introduction flow path L3, but may be one not having the atmosphere introduction flow path if it does not have them.

In addition, the atmosphere is not necessarily required to be introduced into the atmosphere introduction port P3 and the atmosphere introduction path 3L5. For example, oxygen or ozone may be supplied from a cylinder or a gas other than it may be supplied.

In the above-described embodiment, the data on the pressure correction factors is stored in the internal memory of the exhaust gas analysis apparatus, but the data on the pressure correction factors may be stored in an internal memory of an information processing unit as a separate body from the exhaust gas analysis apparatus, and the information processing unit may acquire pieces of analysis data from the respective analyzers of the exhaust gas analysis apparatus and make pressure corrections.

The calibration method of the above-described embodiment is one that performs the zero/span calibration (Step S3), but may not perform the zero/span calibration.

Further, the pressure correction factors may be prepared using, in addition to the pressure at the time of calibration curve preparation, pressure at the time of the zero/span calibration as the reference pressure.

Also, a pressure varying device different from that of the above-described embodiment may be connected to any of the sample gas introduction port, gas discharge port, and atmosphere introduction port of the gas analysis apparatus. In addition, pressures at the respective ports may be regulated to the same pressure by controlling the pressure varying device.

Further, the above-described embodiment describes the exhaust gas analysis apparatus of a vehicle-mounted type, but the exhaust gas analysis apparatus may be not of a vehicle-mounted type but of a stationary type. Also, the analysis target of the exhaust gas analysis apparatus is not limited to the exhaust gas of a vehicle, but may be another type of exhaust gas or environmental gas.

Besides, various modifications and combinations of the embodiments may be made without departing from the scope of the present invention.

REFERENCE SIGNS LIST

100: Gas analysis system
2: Exhaust gas analysis apparatus
25: Suction pump (pump)
P1: Sample gas introduction port
P2: Gas discharge port
P3: Atmosphere introduction port
3: Pressure varying device
31: Pump
32: Buffer tank
3L1: First flow path
3L2: Second flow path
3L3: Third flow path
3L4: Atmosphere introduction path

The invention claimed is:

1. A calibration method for a gas analysis apparatus, comprising:
   connecting a pressure varying device to both a sample gas introduction port and a gas discharge port of the gas analysis apparatus;
   depressurizing both the sample gas introduction port and the gas discharge port to a same pressure by the pressure varying device;
   introducing calibration gas having a known concentration from a calibration gas introduction port of the gas analysis apparatus in a depressurized state; and
   calculating a pressure correction factor for the gas analysis apparatus with use of (i) measurement result of the calibration gas by the gas analysis apparatus and (ii) the known concentration.

2. The calibration method for a gas analysis apparatus according to claim 1, further comprising:
   depressurizing both the sample gas introduction port and the gas discharge port to multiple pressures by the pressure varying device; and
   calculating the pressure correction factor for the gas analysis apparatus so that a measurement result of the calibration gas at each of the multiple pressures becomes equal to a measurement result of the calibration gas at a predetermined reference pressure.

3. The calibration method for a gas analysis apparatus according to claim 2, wherein the predetermined reference pressure is pressure at time of preparing a calibration curve for the gas analysis apparatus or pressure at time of zero and span calibration.

4. The calibration method for a gas analysis apparatus according to claim 1, further comprising:
   introducing an excessive amount of the calibration gas from the calibration gas introduction port; and
   measuring the calibration gas while making the calibration gas overflow from the sample gas introduction port.

5. The calibration method for a gas analysis apparatus according to claim 1, further comprising:
   introducing calibration gases for respective multiple measurement target components; and
   calculating pressure correction factors for the respective multiple measurement target components.

6. The calibration method for a gas analysis apparatus according to claim 5, further comprising:

mixing and introducing the calibration gases for the respective multiple measurement target components; and calculating the pressure correction factors for the respective multiple measurement targets.

7. The calibration method for a gas analysis apparatus according to claim 1, wherein the gas analysis apparatus includes an atmosphere introduction port, further comprising:

connecting the pressure varying device to the atmosphere introduction port; and depressurizing both the sample gas introduction port and the gas discharge port to a same pressure.

8. The calibration method for a gas analysis apparatus according to claim 1, wherein the gas analysis apparatus is of a vehicle-mounted type.

9. A pressure correction method for a gas analysis apparatus, comprising:

with use of the pressure correction factor obtained by the calibration method according to claim 1, correcting a measurement result of actual measurement by the gas analysis apparatus to a measurement result at reference pressure for the gas analysis apparatus on a basis of pressure at time of the actual measurement.

10. An inspection method for a gas analysis apparatus, comprising:

connecting a pressure varying device to both a sample gas introduction port and a gas discharge port of the gas analysis apparatus having a pressure correction function using a pressure correction factor;

depressurizing both the sample gas introduction port and the gas discharge port to a same pressure by the pressure varying device;

introducing calibration gas having a known concentration from a calibration gas introduction port of the gas analysis apparatus in a depressurized state; and comparing a measured value after correction using the pressure correction factor for the gas analysis apparatus and the known concentration of the calibration gas at reference pressure.

11. A gas analysis system comprising:

a gas analysis apparatus configured to analyze a measurement target component in sample gas, and to calculate a pressure correction factor with use of (i) a measurement result of calibration gas having a known concentration which is introduced into the gas analysis apparatus via a calibration gas introduction port in a depressurized state and (ii) the known concentration; and a pressure varying device configured to vary pressure of the gas analysis apparatus, wherein the pressure varying device includes a first flow path whose one end is configured to be connected to a sample gas introduction port of the gas analysis apparatus, a second flow path whose one end is configured to be connected to a gas discharge port of the gas analysis apparatus, and a pump configured to depressurize both the sample gas introduction port and the gas discharge port to a same pressure via the first flow path and the second flow path.

12. The gas analysis system according to claim 11, wherein the first flow path and the second flow path are connected to the pump via a merged flow path.

13. The gas analysis system according to claim 12, further comprising:

an atmosphere introduction path for introducing atmosphere into the merged flow path; and in the atmosphere introduction path, a pressure regulation part that regulates pressures in the first flow path and the second flow path.

14. The gas analysis system according to claim 11, further comprising a third flow path whose one end is to be connected to an atmosphere introduction port of the gas analysis apparatus, wherein the pump is further configured to depressurize the atmosphere introduction port via the third flow path.

* * * * *